United States Patent [19]

McGinley et al.

[11] Patent Number: 4,462,839

[45] Date of Patent: Jul. 31, 1984

[54] ENTERIC COATING FOR PHARMACEUTICAL DOSAGE FORMS

[75] Inventors: Emanuel J. McGinley, Morrisville; Domingo C. Tuason, Jr., Bensalem, both of Pa.

[73] Assignee: FMC Corporation, Philadelphia, Pa.

[21] Appl. No.: 504,779

[22] Filed: Jun. 16, 1983

[51] Int. Cl.$^3$ .......................... C08L 1/08; A01N 25/00
[52] U.S. Cl. .................................... 106/198; 106/194; 424/35; 424/128; 523/204; 536/64; 536/38
[58] Field of Search ............... 106/170, 171, 178, 194, 106/198, 308 Q; 424/35, 128; 536/64, 38; 523/340, 204; 524/414, 904; 427/222

[56] References Cited

U.S. PATENT DOCUMENTS

| | | | |
|---|---|---|---|
| 2,740,723 | 4/1956 | Voris | 106/196 |
| 2,759,925 | 8/1956 | Hiatt | 536/64 |
| 2,800,463 | 7/1957 | Morrison | 523/309 |
| 2,843,582 | 7/1958 | Voris | 536/38 |
| 2,843,583 | 7/1958 | Voris | 536/38 |
| 3,539,365 | 10/1970 | Durand et al. | 106/197 |
| 3,909,444 | 9/1975 | Anderson et al. | 427/222 |
| 3,935,326 | 1/1976 | Groppenbacher et al. | 427/3 |
| 4,112,215 | 9/1978 | Boessler et al. | 528/503 |
| 4,177,177 | 12/1979 | Vanderhoff et al. | 523/300 |
| 4,258,179 | 3/1981 | Kawata | 106/170 |
| 4,287,221 | 9/1981 | Tonedachi et al. | 106/197 |
| 4,309,406 | 1/1982 | Guley | 424/35 |
| 4,330,338 | 5/1982 | Banker | 106/197 C |
| 4,377,568 | 3/1983 | Chopra | 424/31 |
| 4,385,078 | 5/1983 | Onda et al. | 106/170 |

FOREIGN PATENT DOCUMENTS 2057876 4/1981 United Kingdom .

*Primary Examiner*—Theodore Morris
*Attorney, Agent, or Firm*—C. H. Johnson; C. Egolf

[57] ABSTRACT

The application discloses a process for making a polymeric powder which is readily dispersible in water to provide a composition useful for forming an enteric coating on pharmaceutical dosage forms and also a process for using the powder for its intended purpose.

20 Claims, No Drawings

ENTERIC COATING FOR PHARMACEUTICAL DOSAGE FORMS

This invention relates to a polymeric powder which is readily dispersible in water to make a composition useful for providing enteric coatings on pharmaceutical dosage forms such as tablets, pills, capsules, powders, granules and beads. More particularly, the invention relates to such a polymeric powder wherein very small spherical powder particles are aggregated together and when stirred in water with mild agitation readily break up and allow the individual particles to disperse. The invention also relates to a process for making such a powder and to a process for utilizing the same.

As used herein the term "polymeric powder" means a powder the individual particles of which are aggregates of spherical polymer particles providing enteric functionality but which aggregates may also comprise other ingredients such as plasticizer, emulsifying agent and/or a dispersion stabilizer, color, etc. Such aggregates are referred to herein as "powder particles".

Pharmaceutical dosage forms such as tablets and the like commonly consist of a core containing one or more pharmacologically active ingredients together with various excipients which serve as binding agents, disintegrants, etc. The core may be provided with some form of a coating which may serve a variety of purposes such as rendering the dosage more palatable, improving the appearance, controlling release of the active ingredient both as to time and place, and/or for ease of identification. Coatings which are insoluble in the gastric juices of the stomach but which dissolve in the alkaline environment of the intestines are known and are needed for a variety of medical reasons not germane to the present invention. Such coatings are variously referred to as enteric coatings or enterosoluble coatings and will be so referred to hereinafter.

There are a number of known enteric materials, the most widely used probably being cellulose acetate phthalate and it is with this polymer that the present invention is particularly concerned. While being water-insoluble under low pH acidic conditions such as normally encountered in the human stomach, cellulose acetate phthalate is readily soluble in the higher pH environment of intestinal juices. Cellulose acetate phthalate is also readily soluble in volatile organic solvents such as acetone, and mixtures of acetone and methanol, acetone and methylene chloride, etc. and until fairly recently coating compositions were formed by dissolving the polymer in organic solvent. This practice of forming a coating composition by dissolving a polymer in organic solvent has also been used with water-insoluble non-enteric polymers such as ethyl cellulose. To the solution are frequently added pigments, surfactants, plasticizers, preservatives, flavors, etc. and the final composition is sprayed or otherwise applied to the dosage form so as to provide a continuous film upon evaporation of the solvent.

There were and are serious problems in using a solvent system for coating tablets and the like. Often the vapors of organic solvents are toxic or flammable and provide a hazard to the operator and to the premises where the coating operation is performed. There are also environmental problems necessitating the use of extensive recovery systems to avoid escape of the vapors into the atmosphere.

Within recent years aqueous coating systems (as opposed to organic solvent systems) have been developed to eliminate the above mentioned and other problems connected with solvent systems. In one of these newer systems water-insoluble polymer particles are dispersed in water to form a pseudolatex coating composition which is applied to the dosage form in any of several known procedures, usually by spraying. A plasticizer is usually incorporated into the dispersion and often a pigment and other materials are added. As the water evaporates, usually being aided by the controlled application of heat, the polymer particles coalesce to form a continuous film coating.

One of the problems that delayed the development of an aqueous system was in producing polymer particles of a size sufficiently small as to form a stable dispersion; that is to say so that the particles will remain suspended in water due to their Brownian motion and/or convection currents, rather than settle out due to gravity. While reasonably good continuous films may be formed from aqueous polymeric compositions having polymer particles up to about 5.0 $\mu$m in greatest dimension, as a general rule the smaller the size of the polymer particles, the better the film. To form a stable dispersion it is essential that the polymer particles be no more than about 0.5 $\mu$m in greatest dimension and for both best dispersion stability and best film forming properties it is desirable that the polymer particles be spherical and between 0.2 and 0.5 $\mu$m in diameter.

Presently known techniques for mechanical particle size reduction have not been successful in producing polymer particles of the preferred size range. There are known emulsion polymerization techniques for forming dispersions having particles of the desired size but these techniques leave potentially physiologically harmful residual monomer in the dispersion and are therefore not entirely satisfactory when the dispersion is to be used for coating pharmaceutical or food products. Moreover, the most desirable enteric coatings are composed of polymers such as cellulose acetate phthalate which are incapable of being emulsion polymerized.

To avoid the problems associated with emulsion polymerization, aqueous polymer dispersions having the requisite particle size and form can be made by dissolving the polymer in a water immiscible organic solvent, and emulsifying the organic solution in water containing at least one nonionic, anionic or cationic emulsifying agent. The crude emulsion is then subjected to comminuting forces sufficient to form a colloidal or near colloidal dispersion of small, even sized spherical polymer particles having a diameter of less than 1.0 $\mu$m, preferably between 0.2 and 0.5 $\mu$m. The organic solvent is stripped from the system by distillation. For more details as to a process for making such a polymer emulsion or dispersion, reference is directed to U.S. Pat. No. 4,177,177 to Vanderhoff et al. The actual method of forming the dispersion is not a part of the present invention and methods other than that described in the Vanderhoff et al. patent may be used, so long as the desired polymer particle size and shape is obtained. U.S. Pat. No. 4,330,338 to Banker teaches the use of aqueous dispersions of various polymers including cellulose acetate phthalate for forming coatings on pharmaceutical dosage forms.

Applicants have found that while aqueous dispersions of some polymers such as ethyl cellulose are chemically stable for relatively long periods of time, perhaps indefinitely, dispersions of cellulose acetate phthalate are not.

The presence of water in the dispersion hydrolyzes the cellulose acetate phthalate and gradually increases the phthalic acid content to beyond acceptable limits for pharmaceutical use. This inability to successfully store cellulose acetate phthalate aqueous dispersions for long periods of time also applies for the same reason to aqueous dispersions of such other known enteric polymers as hydroxypropyl methylcellulose phthalate and polyvinyl acetate phthalate. Not being able to successfully store the polymer dispersion is particularly undesirable in view of the fact that the scale on which the dispersions are typically used is significantly smaller than the scale on which they can be economically manufactured.

Since it is the presence of water that causes the phthalic acid content of the cellulose acetate phthalate to increase with the passage of time, the storage problem may be overcome by having the cellulose acetate phthalate particles in dry powder form, rather than being dispersed in water. Not only is the dry powder chemically stable but it is considerably easier and less expensive to ship than an aqueous dispersion. In addition, the dry powder is less susceptible to harmful effects of extremes of temperature and less susceptible to microbial growth. However, converting an aqueous dispersion of the polymer particles to a dry powder which can be reconstituted in water to near the original particle size range is not a simple matter. As mentioned above, when water is evaporated from the dispersion by any method, the particles coalesce and form a continuous film. This coalescence of the particles of course will occur regardless of the nature of the substrate, if any, from which the water is evaporated. Once the particles have coalesced there is no known way that the coalesced particles can be separated and restored to the submicron spherical size that they had while in dispersion.

According to U.S. Pat. No. 3,539,365 to Durand et al., an aqueous dispersion of non-water soluble beta-1,4 glucan rod like particles of less than 1.0 μm in length are spray dried after first being coated while in dispersion with a water soluble barrier material. Without the barrier, the beta-1,4 glucan particles would irreversibly bond together in aggregates so that the individually beta-1,4 glucan particles could not be redispersed as stable dispersions. The barrier material surrounding each particle prevents direct contact between the beta-1,4 glucan particles and avoids the irreversible bonding of particles. The spray dried particles may be readily redispersed in water to form a stable dispersion. The Durand et al. patent mentions a number of more or less useful barrier materials, all of which are water soluble over a wide range of pH and none of which solubilize the beta-1,4 glucan. The amount and type of water soluble barrier materials described by Durand et al would interfere with the enteric performance of coating compositions of enterosoluble polymers dried by this method.

U.S. Pat. No. 2,800,463 to Morrison describes a process for converting an aqueous polyvinyl acetate emulsion containing emulsifying agents or protective colloids like polyvinyl alcohol, gum tragacanth, gum acacia, etc. into a powder capable of being redispersed in water. All of the protective colloids mentioned by Morrison are water soluble over a wide range of pH. As described, the process involves either spray drying or freeze drying. The spray drying is carried out at temperatures below that at which the polymer particles sinter together. Unlike the present invention, Morrison relies primarily on temperature control, rather than on a barrier material, to prevent polymer particle sintering, fusion or coalescence during spray drying. Additionally, if the Morrison protective colloids were used in quantities sufficient to prevent coalescence of enteric polymer particles during spray drying, the protective colloids would adversely affect enteric performance of films formed from the spray dried compositions. The dried powder is described by Morrison as being useful in various ways such as for manufacture of paint and adhesives. There is no suggestion that the powder be used to make a composition useful for coating pharmaceutical dosage forms and certainly no suggestion that the powder would be useful for enteric coatings.

According to U.S. Pat. No. 4,112,215 to Boessler et al., a dry powder of a polymeric material suitable for use in a solvent coating composition for pharmaceutical dosage forms may be produced by spray drying an aqueous dispersion of certain vinyl copolymers. The spray drying is carried out at a temperature such that the vinyl copolymer particles do not exceed the minimum film-forming temperature of the polymer. This method requires very careful control of the temperature of the air in the spray dryer. As pointed out in said U.S. Pat. No. 4,112,215, the actual air temperature must be chosen depending upon the amount of water in the dispersion as well as upon the known film-forming temperature of the polymer. Other factors not mentioned in the patent but which affect the heating of the polymer particles are the temperature of the water in the dispersion and the size of the particles. As pointed out in the patent, the only way of knowing whether the proper air temperature is used is by examination of the product obtained after completion of the drying operation; obviously not a very desirable circumstance.

Copending application Ser. No. 440,118 filed Nov. 8, 1982 in the names of the present inventors is closely related to the present invention and describes a method of making a cellulose acetate phthalate powder and other enteric polymeric powders capable of being dispersed in water to form, with the addition of a plasticizer, a film-forming coating composition. According to said application an acetylated monoglyceride characterized by being liquid at room temperature is added to a freshly prepared aqueous dispersion of water-insoluble polymer particles and after thorough stirring, the mixture is spray dried to form a powder consisting essentially of spherical cellulose acetate phthalate or other enteric polymer particles held together in aggregates and impregnated by the acetylated monoglyceride. When this spray dried powder is added to water along with a plasticizer and stirred, the aggregates break up and free the polymer particles in the form and near the size they had in the original dispersion.

The present invention achieves the basic goal of the invention of said copending application Ser. No. 440,118; namely, an enteric polymer is dry powder form capable of being readily dispersed in water to provide, with the addition of a suitable plasticizer, a composition useful for forming an enteric coating on pharmaceutical dosage forms. However, the physical composition of the powder of this invention is distinctly different from the powder of application Ser. No. 440,118, and the process of making the same is also distinctly different.

According to the present invention, the aqueous dispersion of substantially spherical cellulose acetate phthalate particles of less than 5.0 μm diameter, preferably of a diameter between about 0.2 μm to 0.5 μm, optionally formed as above described in reference to the patent to Vanderhoff et al. U.S. Pat. No. 4,177,177, is spray dried after having had added thereto a basic salt. As previously mentioned, the purpose of the powder formed by spray drying the dispersion is for redispersion in water to form a composition suitable for use in providing an enteric coating on pharmaceutical dosage forms. Unlike the invention of the Durand et al. U.S. Pat. No. 3,539,365, which uses a water soluble barrier material that does not render the polymer particles water-soluble, and unlike the invention of application Ser. No. 440,148, which uses a water insoluble barrier material that does not render the polymer particles water-soluble, the present invention uses a water soluble material that also renders the polymer praticles partially soluble in water to minimize coalescense during the spray drying of the dispersion, such that redispersion is possible.

According to the present invention, the individual polymer particles of a freshly prepared aqueous dispersion of a water insoluble enteric polymer such as cellulose acetate phthalate are modified by the addition of a basic salt such as trisodium phosphate, tripotassium phosphate, triammonium phosphate, or the like, preferably in solution, and said solution optionally containing quantities of dissolved water-insoluble enteric polymer. It has been found that a phosphate salt in amount of between 1.4 and 7.3% based upon the weight of the dry polymer, with a preferred range of 2.0 to 4.5% produces the desired results. It is believed that upon spray drying of the modified polymer dispersion, the solubilized portion of the polymer particles serves as a barrier to minimize coalescence. During drying, the individual polymer particles become grouped together in small aggregates, but the soluble portion of the particles minimizes irreversible coalescense and also enables the particles to become redispersed in water at a later time. These aggregates, though small, are considerably larger than the primary particles and are much easier to collect in the spray dryer. If insufficient amounts of phosphate salts were used, resulting in an insufficient quantity of barrier material, the primary polymer particles would easily coalesce during spray drying and therefore could not be redispersed in water. If excessive amounts of phosphate salts were used the amount of water soluble material contained in the composition would adversely affect the enteric performance of a film formed from said composition.

The powder formed is chemically and physically stable thus permitting long term storage. The addition of the phosphate salt solution and subsequent spray drying must of course be done before the aforementioned hydrolysis raises the phthalic acid content to beyond acceptable limits, defined by U.S.P. XX to be 6% by weight of the polymer. The expression "freshly prepared" is used herein in reference to the aqueous dispersion of a water-insoluble enteric polymer during that period prior to the unacceptable increase of phthalic acid content.

When the pharmaceutical manufacturer is ready to use the powder for forming an enteric composition for coating tablets or the like, the powder is added to water, followed by the addition of a suitable plasticizer such as dibutyl sebacate, diethyl phthalate, tributyl citrate, triglycerylacetate, propylene glycol, castor oil, triacetin, polyethylene glycol or mixture of these or other pharmaceutically acceptable plastizers. The plasticizer is preferably used in an amount of between 10% and 40% by weight of the dry polymer. If desired, pigments, flavorings and/or preserving agents may also be added. Upon stirring, the aggregates break up to free the polymer particles in the form and near the size they had in the original dispersion. The water soluble portion or "skin" of the polymer particles serves as a dispersant enabling easy dispersion of the water insoluble polymer particles.

It is believed that the following specific examples will be helpful in understanding and carrying out the invention:

EXAMPLE I 24 g of tripotasium phosphate was dissolved in 1176 g of distilled water. The resulting tripotasium phosphate solution was slowly added to 3920 g of an aqueous cellulose acetate phthalate dispersion containing 848 g of cellulose acetate phthalate polymer, mixed for 1 hr. and passed through a Manton Gaulin Homogenizer at 5500 psi (approximately 37.921 mPa) first stage, 500 psi (approximately 3.447 mPa) second stage and spray dried to form a powder. The spray drying was performed as follows: The homogenized slurry was fed to a 3 foot (0.9144m) Bowen spray dryer utilizing nozzle atomization 0.01 inch (0.000254m) opening. The slurry was fed to the dryer by means of a variable feed Moyno pump at a rate of 70 g/minute. The operating inlet/outlet air temperature of the spray dryer was about 155° C./100° C. 837 g of dry powder was collected per hour having a moisture content of 1.8% and a bulk density of 25.7 lbs/ft$^3$. 305.5 g of spray dried powder ws added to 1630 g of water and mixed for 15 minutes with mild agitation. 60 g of diethyl phthalate plasticizer was slowly added to the aqueous dispersion and mixed for 1 hr. The coating system so prepared was sprayed onto 2 kg of tumbling placebo tablets in a 16" conventional coating pan apparatus utilizing intermittent spray by means of a Graco pump. Film coating on the tablets measured 8–9% based upon the dry weight of the tablet. These tablets were tested in accordance with U.S.P. XX enteric disintegration procedures. The tablets possessed a smooth elegant coating and remained intact in water and gastric fluids and disintegrated in simulated intestinal fluids in about 15 minutes.

EXAMPLE 2

30 g of trisodium phosphate was dissolved in 1470 g of distilled water. The resulting trisodium phosphate solution was slowly added to 4,105 g of an aqueous cellulose acetate phthalate dispersion containing 847 g of cellulose acetate phthalate polymer, mixed for 1 hr. and passed through a Manton Gaulin Homogenizer at 5500 psi (approximately 37.921 mPa) first stage, 500 psi (approximately 3.447 mPa) second stage and spray dried to form a powder. The spray drying was performed as follows: The homogenized slurry was fed to a 3 foot (0.9144 m) Bowen spray dryer utilizing nozzle atomization 0.01 inch (0.000254 m) opening. The slurry was fed to the dryer by means of a variable feed Moyno pump at a rate of 65 g/minute. The operating inlet/outlet air temperature of the spray dryer was about 155° C./96° C. 735 g of dry powder was collected per hour having a moisture content of 1.6% and a bulk density of 23.5 lbs/ft$^3$. 259 g of spray dried powder was added to 1220 g of distilled water and mixed for 15 minutes with mild agitation. 89.25 g of diethyl phthalate was slowly added to the aqueous dispersion and mixed for 1 hr. The coating system so prepared was sprayed onto 2 kg of tumbling placebo tablets in a 16" conventional coating pan apparatus utilizing intermittent spray by means of a Graco pump. Film coating on the tablets measured 8–9% based upon the dry weight of the tablet. These tablets were tested in accordance with U.S.P. XX enteric disintegration procedure. The tablets possessed a smooth elegant coating and remained intact in water and gastric fluids and disintegrated in simulated intestinal fluids in about 15 minutes.

EXAMPLE 3

42.5 g of trisodium phosphate was dissolved in 2082.5 g of distilled water. An aqueous solution of cellulose acetate phthalate was prepared by slowly adding 50 g of cellulose acetate phthalate polymer to 625 g of the trisodium phosphate solution and mixed until all of the polymer was completely dissolved. Solution time was 50 minutes.

In another vessel, the remaining 1500 g of the above trisodium phosphate solution was slowly added to 3167 g of an aqueous cellulose acetate phthalate dispersion containing 686 g of cellulose acetate phthalate polymer, and mixed for 1 hr.

The 675 g aqueous solution of the sodium salt of cellulose acetate phthalate prepared as described above was then carefully added to the aqueous dispersion of cellulose acetate phthalate treated with trisodium phosphate, mixed for 1 hr. and passed through a Manton Gaulin Homogenizer at 5500 psi (approximately 37.921 mPa) first stage, 500 psi (approximately 3.447 mPa) second stage and spray dried to form a powder. The spray drying was performed as follows: The homogenized slurry was fed to a 3 ft. (0.9144 m) Bowen spray dryer utilizing nozzle atomization 0.01 in. (0.000254 m) opening. The slurry was fed to the dryer by means of a variable feed Moyno pump at a rate of 82 g/minute. The operating inlet/outlet temperature of the spray dryer was about 145° C./87° C. 804 g of dry powder was collected per hour having a moisture content of 2.0% and a bulk density of 21.5 lbs/ft$^3$. 306 g of spray dried powder was added to 1436 g of distilled water and mixed for 15 minutes with mild agitation. 105 g of diethyl phthalate was slowly added to the aqueous dispersion and mixed for 1 hour. The coating system so prepared was sprayed onto 2 kg of tumbling placebo tablets in a 16" conventional coating pan apparatus utilizing intermittent spray by means of a Graco pump. Film coating on tablets measured 8–9% based upon the dry weight of the tablet. These tablets were tested in accordance with U.S.P. XX enteric disintegration procedure. The tablets possessed a smooth elegant coating and remained intact in water and gastric fluids and disintegrated in simulated intestinal fluids in about 15 minutes.

While the invention has been described specifically in connection with cellulose acetate phthalate, it will be apparent to those skilled in the art that it is equally applicable in principal to other known enteric polymers such as hydroxypropyl methylcellulose phthalate, polyvinyl acetate phthalate, and the like.

Having thus described the invention, what is claimed is:

1. A process of making a polymeric powder which is readily dispersible in water to provide a composition useful for forming an entric coating on pharmaceutical dosage forms, comprising providing a freshly prepared aqueous dispersion of spherical water-insoluble enteric polymer particles, adding to said dispersion a phosphate salt in an amount sufficient to minimize coalescense of the particles during spray drying, thoroughly mixing, and spray drying to form the powder.

2. The process set forth in claim 1 wherein the phosphate salt is either trisodium phosphate, tripotassium phosphate or triammonium phosphate.

3. The process set forth in claim 1 wherein the phosphate salt is added in an amount of between about 1.4% and about 7.3% based upon the weight of the dry insoluble polymer particles.

4. The process set forth in claim 1 wherein the phosphate salt is added in an amount of between about 2.0% and about 4.5% based upon the weight of the dry insoluble polymer particles.

5. The process set forth in claim 1 wherein said polymer particles predominantly have a diameter below 5.0 $\mu$m.

6. The process set forth in claim 5 wherein said polymer particles predominantly have a diameter between about 0.2 and 0.5 $\mu$m.

7. The process set forth in claim 6 wherein the spray dried powder consists of aggregates of particles capable of being reconstituted to near the original size of the solid particles contained in the freshly prepared aqueous dispersion.

8. The process set forth in claim 7 comprising the additional steps of dispersing the spray dried powder in water, adding a plasticizer in an amount of between 10% and 40% of the weight of the dry polymer to form a coating composition, and coating a pharmaceutical dosage form therewith.

9. A polymeric powder made by the process of claim 1.

10. A process of making a polymeric powder which is readily dispersible in water to provide a composition useful for forming an enteric coating on pharmaceutical dosage forms, comprising providing a freshly prepared aqueous dispersion of cellulose acetate phthalate particles, adding to said dispersion a phosphate salt in an amount sufficient to minimize coalescense of the particles during spray drying, thoroughly mixing, and spray drying to form the powder.

11. The process set forth in claim 10 wherein the phosphate salt is either trisodium phosphate, tripotassium phosphate or triammonium phosphate.

12. The process set forth in claim 10 wherein the phosphate salt is added in an amount of between about 1.4% and about 7.3% based upon the weight of the dry cellulose acetate phthalate particles.

13. The process set forth in claim 10 wherein the phosphate salt is added in an amount of between about 2.0% and about 4.5% based upon the weight of the dry cellulose acetate phthalate particles.

14. The process set forth in claim 10 wherein said cellulose acetate phthalate particles are spherical and predominantly have a diameter below 5.0 $\mu$m.

15. The process set forth in claim 14 wherein said cellulose acetate phthalate particles predominantly have a diameter between about 0.2 and 0.5 $\mu$m.

16. The process set forth in claim 15 wherein the spray dried powder consists of aggregates of particles capable of being reconstituted to near the original size of the solid particles contained in the freshly prepared aqueous dispersion.

17. The process set forth in claim 16 comprising the additional steps of dispersing the spray dried powder in water, adding a plasticizer in an amount of between 10% and 40% of the weight of the cellulose acetate phthalate particles to form a coating composition, and coating a pharmaceutical dosage form therewith.

18. A polywmeric powder made by the process of claim 10.

19. A polymeric powder capable of being readily dispersed in water to provide with the addition of a plasticizer a composition useful for forming an enteric coating on pharmaceutical dosage forms, said powder consisting essentially of spherical water-insoluble enteric polymer particles, said enteric polymer particles having a water-insoluble core of such polymer and a water soluble surface portion of such polymer.

20. The powder set forth in claim 19 wherein said polymer is cellulose acetate phthalate.

* * * * *